United States Patent [19]
Grother et al.

[11] Patent Number: 6,156,339
[45] Date of Patent: Dec. 5, 2000

[54] PROCESS FOR PREPARING SOLID PHARMACEUTICAL DOSAGE FORMS

[75] Inventors: Leon Grother; Michael Hall, both of Swindon; Douglas Bryans, Easterton; Richard Green, Manton; Patrick Kearney, Toothill, all of United Kingdom

[73] Assignee: R.P. Scherer Corporation, Basking Ridge, N.J.

[21] Appl. No.: 09/387,702

[22] Filed: Aug. 10, 1999

Related U.S. Application Data

[63] Continuation of application No. PCT/GB98/00425, Feb. 12, 1998.

[30] Foreign Application Priority Data

Feb. 12, 1997 [GB] United Kingdom .................. 9702799

[51] Int. Cl.⁷ .................................................. A61K 9/127
[52] U.S. Cl. ........................... 424/450; 264/4.1; 424/489; 424/490; 424/450; 424/469; 424/470; 424/451; 424/502; 424/493; 424/494; 424/500; 424/497; 424/499
[58] Field of Search ...................... 424/489, 490, 424/484, 450, 469, 470, 451, 502, 493, 494, 500, 497, 499; 264/4.1

[56] References Cited

U.S. PATENT DOCUMENTS 5,738,875  4/1998  Yarwood et al. ....................... 424/484
5,853,762 12/1998  Myers et al. ........................... 424/488

FOREIGN PATENT DOCUMENTS

| 0 078 215 A2 | 10/1982 | European Pat. Off. . |
| 0 159 237 A1 | 3/1985 | European Pat. Off. . |
| 0 409 432 A2 | 6/1990 | European Pat. Off. . |
| 0 450 141 A1 | 8/1990 | European Pat. Off. . |
| 85/05029 | 11/1985 | WIPO . |
| WO 92/21328 | 12/1992 | WIPO . |
| 96/13251 | 5/1996 | WIPO . |
| 96/13252 | 5/1996 | WIPO . |

*Primary Examiner*—Thurman K. Page
*Assistant Examiner*—Liliana Di Nola-Baron
*Attorney, Agent, or Firm*—Andrew G. Rozycki; Donald O. Nickey; Robert W. Diehl

[57] ABSTRACT

This invention relates to a process for the preparation of an oral solid rapidly disintegrating dosage form of a pharmaceutically active substance which has an unacceptable taste which process comprises: (i) forming a solution or a suspension in a solvent of a water soluble or water dispersible carrier, a filler and the pharmaceutically active substance with the unacceptable taste in association with a lipid, the weight ratio of the pharmaceutically active substance to the lipid being in the range of from 1:1 to 1:10 and the weight ratio of the carrier to the lipid being in the range of from 5:1 to 1:15; (ii) forming discrete units of the suspension or solution; and (iii) removing the solvent from the discrete units under conditions whereby unit dosages are formed comprising a network of carrier/filler carrying a dosage of the pharmaceutically active substance in association with the lipid; oral solid rapidly disintegrating dosage forms prepared by such a process are also provided.

34 Claims, No Drawings

PROCESS FOR PREPARING SOLID PHARMACEUTICAL DOSAGE FORMS

This Application is a continuation of International Application No. PCT/GB98/00425, filed Feb. 12, 1998, now pending (which is hereby incorporated by reference.)

FIELD OF THE INVENTION

The present invention relates to a process for preparing solid pharmaceutical dosage forms and, in particular, to a process for preparing an oral solid rapidly disintegrating dosage form of a pharmaceutically active substance which has an unacceptable taste to a human being or to an animal, and to solid pharmaceutical dosage forms prepared thereby.

BACKGROUND OF THE INVENTION

Many pharmaceutically active substances are presented for oral administration in the form of tablets, pills or capsules. The tablet, pill or capsule generally has to be swallowed with water so that the pharmaceutically active substance can be absorbed via the gastro intestinal tract. For some patients swallowing the tablet, pill or capsule is difficult or impossible and this is particularly the case for paediatric patients and geriatric patients. A similar difficulty is often encountered when trying to administer tablets to non-human animals which may be uncooperative in taking tablets, pills or capsules.

Oral solid pharmaceutical dosage forms which rapidly disintegrate in the mouth and methods for their preparation have been proposed in GB-A-1548022 and GB-A-2111423. The solid dosage forms as disclosed comprise an open matrix network carrying the pharmaceutically active substance, the open matrix comprising a water-soluble or water-dispersible carrier material which is inert towards the pharmaceutically active substance. The solid dosage forms are prepared by the sublimation or removal of solvent from a solution or suspension comprising the pharmaceutically active substance and the carrier material. Sublimation or removal of solvent is preferably carried out by freeze drying.

Other methods for the preparation of oral solid pharmaceutical dosage forms which rapidly disintegrate in the mouth are disclosed in EP-A-0627218, U.S. Pat. No. 4,855,326, U.S. Pat. No. 5,039,540, U.S. Pat. No. 5,079,018, U.S. Pat. No. 5,120,549, U.S. Pat. No. 5,298,261, U.S. Pat. No. 5,330,763, U.S. Pat. No. 5,587,180, WO 91/04757 (PCT/US90/05206), WO 93/12769 (PCT/JP93/01631) and PCT/US93/12566.

The solid dosage forms which are produced by these various methods rapidly disintegrate on being placed in the mouth of the patient, thereby delivering the desired dose of the pharmaceutically active substance.

Although the solid dosage forms as described above overcome the problem of swallowing tablets, pills or capsules, the patient will taste the pharmaceutically active substrate as the dosage form disintegrates. For some pharmaceutically active substances the taste, if slightly unpleasant, can be rendered acceptable by the use of sweetening agents or flavouring agents which mask the taste. However, for some pharmaceutically active substances an unpalatable product will still be produced, despite the use of sweetening agents and flavouring agents, which decreases patient compliance.

In WO-A-96/13252, we have described a process for the preparation of an oral solid rapidly disintegrating dosage form of a pharmaceutically active substance having an unacceptable taste, the process involving presenting the pharmaceutically active substance in the network of carrier material in a form which is less soluble in water and more palatable than the form with the unacceptable taste.

Whilst the use of lipids to tastemask or modify drug release has been proposed in the prior art, for example WO-A-94/05260 and WO-A-94/25006, the compositions disclosed therein are liquid dosage forms which include high levels of sweeteners, such as sucrose. In these liquid dosage forms the lipid coats the drug particles to form a physical barrier to delay release of the drug. Such compositions cannot be formed into freeze dried dosage forms since release of the drug would occur during the aqueous suspension stage.

EP-A-0631787 describes the use of acidic phospholipids for the suppression of bitter taste in foods, toiletries or in pharmaceutical compositions such as capsules, granules, liquids or syrups.

SUMMARY OF THE INVENTION

We have now developed a process for preparing oral solid rapidly disintegrating dosage forms of drugs which have an unpleasant or bitter taste which involves the use of a novel combination of a lipid and particular structure forming agents in such dosage forms which complexes with the drug during the mixing step. The drug remains associated with the lipid after freeze drying and upon redispersion the drug is prevented from coming into contact with the mucosa and the taste is masked.

Accordingly, the present invention provides a process for the preparation of an oral solid rapidly disintegrating dosage form of a pharmaceutically active substance which has an unacceptable taste which process comprises:

(i) forming a solution or a suspension in a solvent of a water soluble or water dispersible carrier, a filler and the pharmaceutically active substance with the unacceptable taste in association with a lipid, the weight ratio of the pharmaceutically active substance to the lipid being in the range of from 1:1 to 1:10 and the weight ratio of the carrier to the lipid being in the range of from 5:1 to 1:15;

(ii) forming discrete units of the suspension or solution; and (iii) removing the solvent from the discrete units under conditions whereby unit dosages are formed comprising a network of carrier/filler carrying a dosage of the pharmaceutically active substance in association with the lipid.

DETAILED DESCRIPTION OF THE INVENTION

By the term "rapidly disintegrating" as used herein is meant that the solid dosage form will disintegrate in water at 37° C. in 60 seconds or less, preferably 5 to 10 seconds or less when tested by the following procedure which is analogous to the Disintegration Test for Tablets, B.P. 1973 and which is described in British Patent No. 1548022:

Apparatus

A glass or suitable plastic tube 8 to 100 mm long, with an internal diameter of about 28 mm and an external diameter of 30 to 31 mm, and fitted at the lower end, so as to form a basket, with a disc of rustproof wire gauze complying with the requirements for a No. 1.70 sieve (B.P. 1973 page A136).

A glass cylinder with a flat base and an internal diameter of about 45 mm containing water and not less than 15 cm deep at a temperature between 36° and 38° C.

The basket is suspended centrally in the cylinder in such a way that it can be raised and lowered repeatedly in a uniform manner so that at the highest position the gauze just breaks the surface of the water and at the lowest position the upper rim of the basket just remains clear of the water.

Method

Place one shaped article in the basket and raise and lower it in such a manner that the complete up and down movement is repeated at a rate equivalent to thirty times a minute. The shaped articles are disintegrated when no particle remains above the gauze which would not readily pass through it.

On oral administration of the solid dosage form of the invention to a patient the pharmaceutical dosage form rapidly disintegrates in the mouth.

The oral rapidly disintegrating solid dosage form of the present invention enables poorly tasting pharmaceutically active substances to be presented in a palatable form without significantly changing the dispersion characteristics of the oral rapidly disintegrating solid dosage form.

In carrying out the process of the present invention the carrier is generally incorporated into the solution or suspension in an amount of from 1 to 6% by weight, preferably in an amount of from 1.5 to 4% by weight. Suitable water soluble or water dispersible carrier method which may be used in the present invention include materials derived from animal or vegetable proteins, such as the gelatins, dextrins and soy, wheat and psyllium seed proteins; gums such as acacia, guar, agar and xanthan; polysaccharides; alginates; carboxymethylcelluloses; carrageenans; dextrans; pectins; synthetic polymers such as polyvinylpyrrolidone; and polypeptide/protein or polysaccharide complexes such as gelatin-acacia complexes. Gelatin is particularly preferred for use.

The filler is generally incorporated into the solution or suspension in an amount of from 1 to 6% by weight, preferably in an amount of from 1.5 to 4% by weight. Suitable fillers for use in the invention include sugars such as mannitol, sorbitol, xylitol, dextrose, lactose and galactose; cyclic sugars such as cyclodextrin; inorganic salts such as sodium phosphate, sodium chloride and aluminium silicates; and amino acids having from 2 to 12 carbon atoms such as glycine, L-alanine, L-aspartic acid, L-glutamic acid, L-hydroxyproline, L-isoleucine, L-leucine and L-phenylalanine. Mannitol is particularly preferred for use.

Preferred ratios of carrier to lipid are within the range of 5:1 to 1:15.

The lipids which can be used in the present invention include waxes such as beeswax, carnauba wax, or lanolin; saturated or non-saturated fatty acids (preferably $C_{10}$–$C_{30}$) such as stearic acid or oleic acid; derivatives of such fatty acids such as sodium stearyl fumarate and glycerol esters including mono-, di- or triglycerides such as glyceryl monostearate, glyceryl palmitostearate or mixtures thereof, lecithins such as soybean lecithin or egg lecithin; phospholipids or lysophospholipids including phosphatidylcholine, phosphatidylethanolamine, phosphatidylinositol, phosphatidylserine, phosphatidic acid and mixtures thereof; glycolipids such as cerebroside; sterols such as cholesterol; oils such as mineral oil, cotton seed oil, castor oil, soybean oil, peanut oil and coconut oil; hydrogenated vegetable oil; fatty hydrocarbons or alcohols (preferably $C_{10}$–$C_{30}$); or any mixtures or combinations thereof.

In one aspect of the invention, it is preferred that the lipid is a wax, a saturated or non-saturated fatty acid or a derivative thereof (especially stearic acid or a derivative thereof), a triglyceride, an oil, or a $C_{10}$–$C_{30}$ aliphatic alcohol. In another aspect, it is preferred that the lipid is a lecithin or phospholipid or a glycolipid and, in a further aspect, it is preferred that the lipid is a sterol.

The process of the present invention allows the in-situ association of the pharmaceutically active substance with the lipid to form an association which is stable throughout the drying process as the carrier/filler network is formed. The association between the pharmaceutically active substance and the lipid may either be as a result of the partitioning of the pharmaceutically active substance into the lipid structures, by direct binding of the pharmaceutically active substance to the lipid molecules or by adsorption of the pharmaceutically active substance onto the surface of the insoluble lipid particles. Different interactions will occur depending on the physicochemical properties of the drug and of the lipid. Drugs with high lipid solubility or a high log P are likely to interact due to a partitioning effect into the lipid region. For charged drugs, an ion pair interaction can occur with oppositely charged lipid molecules or surface binding can occur with lipid particles. Suitable lipids can therefore be selected to maximise the extent of the interaction. The carrier and filler are responsible for forming the network of material which carries the dosage of the pharmaceutically active substance complexed with the lipid in the dried dosage form. Some carriers, such as gelatin also act as an emulsifying agent which enables the lipid material to be effectively dispersed.

When the oral solid dosage forms of a pharmaceutically active substance produced according to the process of the invention are taken orally, the lipid prevents the pharmaceutically active substance from coming into contact with the mucosa and the taste is masked as the dosage form is taken.

It will be understood that different lipid/pharmaceutically active combinations may be chosen so as to optimise the degree of association and thereby to obtain the most beneficial taste masking effect.

The process of the present invention has advantage over the prior art processes in which the lipid provides a physical barrier or coating. As the pharmaceutically active substance is complexed with the lipid by one of the three mechanisms described above, it does not gradually release over the time necessary to process and dose a batch. Physical coatings tend to swell and erode with time, or the drug can diffuse through the coating into the aqueous solution. Thus, whereas the prior art processes have been suitable for use with drugs with high lipid solubility, the process of the present invention can also be used with water soluble pharmaceutically active substances.

The amount of pharmaceutically active substance contained within each unit dosage will depend upon the drug characteristics but may be up to 100 mg per unit dosage, at levels of up to 25% by weight of the suspension or solution used in the preparation of the unit dosages in accordance with the process of the invention. The amount of lipid required depends upon the degree of binding, the taste of the pharmaceutically active substance and the desired release characteristics, but can generally be included in an amount of up to 250 mg of lipid per unit dosage, at levels of up to 25% by weight of the suspension or solution used in the process of the invention.

Classes of pharmaceutically active substances which may be formulated in the process of the present invention include antacids, analgesics, anti-anginals, anti-anxiety drugs, anti-arrhythmics, anti-bacterials, anti-diarrhoeals, antidepressants, anti-epileptics, anti-fungals, anti-histamines, anti-hypertensives, anti-inflammatory agents, anti-virals, cardiac agents, contraceptives, cough suppressants, cytotoxics, decongestants, diuretics, drugs for genito-urinary disorders, drugs for use in parkinsonism and related disorders, drugs for use in rheumatic disorders, hypnotics, minerals and vitamins, lipid lowering drugs and sex hormones.

This list is not intended to be exhaustive, but demonstrates the wide applicability of this technique in tastemasking or modifying the release of any pharmaceutical agent. This technique is also intended to apply to any pharmaceutically acceptable salt form of a medicament.

The carrier to lipid ratio used in the process of the present invention is within the range of from 1:1 to 1:10 by weight and will depend upon the amounts of these components required to obtain dosage units, on freeze drying, with suitable properties such as hardness and rapid disintegration times. At low lipid levels greater amounts of carrier are required to maintain suitable properties, whereas at high lipid levels, the carrier content must be reduced, otherwise very hard units may result with slow disintegration times.

The discrete units of the suspension or solution may be in the form of liquid units, for example contained within the pockets of a suitable mould; solid units, for example frozen units; or gelled units depending upon the amount and type of carrier in the composition.

The removal of solvent from the discrete units of the solution or suspension comprising the pharmaceutically active substance is carried out by techniques well known to those skilled in the art.

When the discrete units are in liquid form they will generally be frozen or gelled prior to drying.

The liquid solution or suspension which may be contained within the pockets of a suitable mould is frozen, for example by passing a gaseous cooling medium, such as liquid nitrogen over the mould, or by inserting the mould into a nitrogen spray freezing chamber, or cooling by passing the mould over a cold surface. Once the dosage forms have been frozen, the mould may be stored in a cold store, prior to drying. Frozen discrete units may be dried by freeze drying according to techniques which are well known in the art. The solvent is sublimed in a freeze drying process under a reduced pressure which transforms the solid solvent directly into a vapour. The freeze drying process will generally be carried out in a freeze drying chamber typically operating under a vacuum of 0.1 to 1.0 mbar for a period of time of from 180 to 500 minutes.

Alternatively, frozen discrete units may be dried by a process as described in U.S. Pat. Nos. 5,120,549 and 5,330,763. In this method the pharmaceutically active substance and carrier material dispersed in a first solvent is solidified and the solidified matrix is subsequently contacted with a second solvent that is substantially miscible with the first solvent at a temperature lower than the solidification point of the first solvent, the matrix component being substantially insoluble in the second solvent, the first solvent thereby being removed from the matrix.

Another alternative process for drying frozen discrete units is described in WO94/14422. In this process the solvent is removed under conditions whereby the solvent is evaporated from the solid through the liquid phase to a gas, rather than subliming from a solid to a gas as in lyophilization. This is achieved by vacuum drying at a temperature below the equilibrium freezing point of the composition at which point the solvent (such as water) changes phase.

When the discrete units are gelled units, any drying methods can be used which do not affect the properties of the preparations. For example, drying may be carried out at decreased pressure, or by forced-air drying. Drying at decreased pressure is preferably carried out at a temperature of from 25° to 35° C. under a vacuum of −750 mm Hg or less, for 2 to 5 hours, whilst drying using forced-air drying is preferably carried out at a temperature of from 3° to 15° C. for 1 to 6 days.

The solvent used in forming the solution or suspension of the pharmaceutically active substance is preferably water but it may be admixed with a co-solvent, such as alcohol, if it is desired to improve the solubility of the active substance.

The suspension or solution prepared according to the process of the present invention is preferably formed into discrete units by introduction into a mould which preferably comprises a plurality of depressions, each depression being of the desired shape and size for the oral dosage form product. The mould preferably comprises a plurality of depressions formed in a sheet of a filmic material which may be similar to the material employed conventionally in the blister packaging of pharmaceuticals. A particularly preferred filmic material for use as a mould in the present invention is described in WO94/12142. The desired quantities of the suspension or solution may be filled into the mould using an automatic filling means which delivers a predetermined dose into each of the depressions in the mould.

A covering material may be adhered to the filmic material in the area surrounding the depressions after the removal of solvent from the solution or suspension filling the depressions. The covering sheet is preferably an aluminium foil or aluminium foil laminate which may be adhered to the filmic material around the depressions by, for example a heat sensitive material. The cover sheet may be adhered to the filmic material in a manner such that it can be peeled away by the user to uncover the oral dosage form in the depression in the mould or, alternatively, it may be adapted for the oral dosage forms to be pushed through.

Alternative methods of forming discrete frozen or gelled units of the solution or suspension include solidifying the mixtures in dropwise fashion. For example, the solution or suspension may be passed through one or more holes to form drops, spheres or a spray of small particles which can be solidified by passage through a cold gas or liquid, for example liquid nitrogen. Alternatively, the drops, spheres or spray may be solidified by contact with a chilled liquid which is immiscible with the solution or suspension and which has a density such that the drops either fall through the immiscible liquid as they solidify, or float on the surface of the immiscible liquid.

The suspension or solution prepared in accordance with the process of the present invention may also contain other additional ingredients such as colouring agents, flavouring agents, sweetening agents or preservatives.

The process of the present invention may be used to prepare oral solid rapidly disintegrating dosage forms of various pharmaceutically active substances which have an unacceptable taste.

The process of the present invention for making more palatable oral rapidly disintegrating dosage forms obviates the need to use costly drug coating techniques or complexation techniques to mask the taste of the pharmaceutically active substance.

The present invention also includes within its scope the oral solid rapidly disintegrating dosage forms prepared according to the process of the invention.

Accordingly, the present invention includes within its scope an oral solid rapidly disintegrating dosage form of a pharmaceutically active substance which has been rendered more palatable by the process as described above.

The present invention will be further described with reference to the following Examples.

Furthermore, the present invention also includes within its scope an oral solid rapidly disintegrating dosage form of a pharmaceutically active substance having an unacceptable taste which comprises a network of a carrier/filler material carrying a dosage of the said pharmaceutically active substance in association with a lipid.

EXAMPLE 1

An oral solid rapidly disintegrating dosage form of dextromethorphan was prepared as follows:

| Ingredients | % by weight |
| --- | --- |
| Purified water | 87.30 |
| Gelatin | 2.40 |
| Mannitol | 1.80 |
| Dextromethorphan HBr | 1.50 |
| Epikuron 200SH* | 6.00 |
| Aspartame | 1.00 |

*EPIKURON 200 SH was supplied by Lucas Meyer and is a purified hydrogenated phosphatidyl-choline of soybean origin comprising at least 98% phosphatidyl choline.

The gelatin and mannitol were added to water in a mixing bowl and heated with mixing to approximately 40° C. The mixture was mixed until dissolution of the gelatin was complete and cooled to 23° C.

Aspartame was added to the gelatin solution before the addition thereto of dextromethorphan HBr by sprinkling the drug into the mix. The Epikuron 200SH was sprinkled into the mix as it was rapidly stirred. The suspension was dosed in 1.0 ml portions into blister pockets, frozen and freeze dried to produce the final dosage form.

The product had an acceptable taste.

EXAMPLE 2

Comparative

An oral solid rapidly disintegrating dosage form of dextromethorphan Hbr was prepared as follows:

| Ingredients | % by weight |
| --- | --- |
| Purified water | 86.50 |
| Gelatin | 4.00 |
| Mannitol | 3.00 |
| Dextromethorphan HBr | 1.50 |
| Glycine | 2.00 |
| Aspartame | 2.00 |
| Mint flavour | 1.00 |

The general procedure of Example 1 was followed with the mint flavour and glycine added to gelatin solution at the same time as the addition of aspartame. After the addition of the dextromethorphan HBr to the mix the suspension was dosed into blister pockets, frozen and freeze dried to produce the final dosage form.

The product had a bitter taste and resulted in a numbing sensation in the mouth.

EXAMPLE 3

An oral solid rapidly disintegrating dosage form of dextromethorphan was prepared as follows:

| Ingredients | % by weight |
| --- | --- |
| Purified water | 86.80 |
| Gelatin | 2.40 |
| Mannitol | 1.80 |
| Dextromethorphan HBr | 1.50 |
| Epikuron 100P** | 7.50 |

**Epikuron 100P was supplied by Lucas Meyer and is a powdered, deoiled soybean lecithin containing a mixture of polar phospholipids and glycolipids (phosphatidyl choline 20–25%, phosphatidylethanolamine 18–22%, phosphatidylinositol 12–15% and phosphatidic acid 5–7%).

The procedure of Example 1 was repeated with the substitution of Epikuron 100P for the Epikuron 200SH.

The product had an acceptable, if rather insipid, taste.

EXAMPLE 4

Comparative

An oral solid rapidly disintegrating dosage form of ketoprofen was prepared as follows:

| Ingredients | % by weight |
| --- | --- |
| Purified water | 91.25 |
| Gelatin | 4.00 |
| Mannitol | 3.00 |
| Ketoprofen | 1.25 |
| Aspartame | 0.50 |

The gelatin and mannitol were dispersed in water and heated to 60° C. to dissolve. After cooling to 25° C. the aspartame was added. Small amounts of the solution were added to the ketoprofen powder to make a paste before adding the remainder of the solution. 1.0 g amounts of the suspension were dosed into blister pockets, frozen and freeze dried as previously described.

When tasted the dried units produced a persistent burning sensation in the throat.

EXAMPLE 5

An oral solid rapidly disintegrating dosage form of ketoprofen was prepared as follows:

| Ingredients | % by weight |
| --- | --- |
| Purified water | 81.55 |
| Gelatin | 2.40 |
| Mannitol | 1.80 |
| Ketoprofen | 1.25 |
| Stearic acid | 12.50 |
| Aspartame | 0.50 |

Stearic acid and ketoprofen were mixed together and heated to 70° C. Gelatin and mannitol were dispersed in water and heated to 60° C. The gelatin was then added to the stearic acid/ketoprofen and homogenised for 5 minutes. The emulsion was then cooled whilst stirring was continued. Aspartame was added to the mix where it had cooled to 25° C. 1.0 ml amounts were dosed, frozen and freeze dried as. previously described. The dried units had a sweet taste.

EXAMPLE 6

Comparative Taste Tests

Dextromethorphan HBr gives a bitter taste or numbing sensation when in contact with the tongue. Five batches of conventional formulations were made containing 0–15 mg of dextromethorphan HBr as follows:

| Ingredients | Batch Composition % w/w | | | | |
|---|---|---|---|---|---|
| | A | B | C | D | E |
| Purified water | 92.0 | 90.5 | 91.25 | 91.625 | 91.812 |
| Gelatin | 4.00 | 4.00 | 4.00 | 4.00 | 4.00 |
| Mannitol | 3.00 | 3.00 | 3.00 | 3.00 | 3.00 |
| Aspartame | 0.50 | 0.50 | 0.50 | 0.50 | 0.50 |
| Mint flavour | 0.50 | 0.50 | 0.50 | 0.50 | 0.50 |
| Dextromethorphan HBr | 0 | 1.50 | 0.75 | 0.375 | 0.188 |

These were tasted by two volunteers in a blind fashion and scored from 0–5 where 0 indicates no bitter taste/numbing sensation and 5 is the most bitter/numbing. This test was performed to assess if the volunteers could differentiate between the dosage of these units. The whole unit was allowed to disperse on the tongue and spat out after a further 10 seconds. Up to two units were tasted each day over a period of a week. After tasting all of these units, the same volunteers were given further units to taste which had the following formulations:

| Ingredients | Batch Composition % w/w | | | | |
|---|---|---|---|---|---|
| | F | G | H | I | J |
| Purified water | 89.00 | 84.40 | 88.15 | 90.40 | 90.40 |
| Gelatin | 2.00 | 3.20 | 3.20 | 3.20 | 3.20 |
| Mannitol | 1.50 | 2.40 | 2.40 | 2.40 | 2.40 |
| Aspartame | 0.00 | 0.50 | 0.50 | 0.50 | 0.50 |
| Mint flavour | 0.00 | 0.50 | 0.50 | 0.50 | 0.50 |
| Dextromethorphan HBr | 0.00 | 1.50 | 1.50 | 1.50 | 1.50 |
| Epikuron 100p | 7.50 | 7.50 | 3.75 | 1.50 | 0 |
| Epikuron 200SH | 0 | 0 | 0 | 0 | 1.5 |

These units were also tasted in a blind fashion and scored in the same manner as formulations A–E. This was done to assess if the presence of Epikuron 100P or 200SH has any taste masking effect.

In a further test, unit F (placebo with 75 mg of Epikuron 100P) was again tasted but this time it was allowed to coat the tongue and then unit B (dextromethorphan 15 mg without any lipid) was tasted without spitting the first unit out. The taste of only the second unit was noted. This test was performed to assess if there is any difference between the taste of this unit and unit G (15 mg of dextromethorphan with 75 mg of Epikuron 100P). If Unit G tastes better than unit F followed by unit B, this would suggest that the inhibitory mechanism of lecithin is an action on the tongue.

Tasting Results

| Formulation | Dextromethorphan (mg/unit) | Lecithin/drug ratio | Score* |
|---|---|---|---|
| A | 0 | — | 1.5 |
| B | 15.0 | — | 4.0 |
| C | 7.50 | — | 2.0 |
| D | 3.75 | — | 2.0 |
| E | 1.88 | — | 0.5 |
| F | 0 | — | 0 |
| G | 15 | 5:1(Epikuron 100P) | 1.75 |
| H | 15 | 2.5:1(Epikuron 100P) | 2.75 |
| I | 15 | 1:1(Epikuron 100P) | 3.75 |
| J | 15 | 1:1(Epikuron 200SH) | 3.75 |
| F + B | 0 + 15 | 5:1(Epikuron 100P) | 3.0 |

*Mean of 2 volunteers' results.

These results demonstrate that
1) Volunteers can differentiate between the different doses of dextromethorphan
2) There is more than a 2-fold reduction in the bitter taste or numbing sensation of a 15 mg Dextromethorphan unit when formulated with a 5:1 ratio of Epikuron 100P.
3) The tastemasking is much less effective when the lecithin is used to coat the tongue prior to taking the 15 mg dose. This suggests that the drug complexes with Epikuron 100P during the production process and that the mechanism is not an action on the tongue taste receptors.
4) Unit J, which contains purified phosphatidyl choline, has no greater taste masking effect than unit I.

What we claim is:

1. A process for the preparation of an oral solid rapidly disintegrating dosage form of a pharmaceutically active substance which has an unacceptable taste which process comprises:

(i) forming a solution or a suspension in a solvent of a water soluble or water dispersible carrier, a filler, the pharmaceutically active substance with the unacceptable taste and a lipid wherein the pharmaceutically active substance forms an association in situ with the lipid, the weight ratio of the pharmaceutically active substance to the lipid being in the range of from 1:1 to 1:10 and the weight ratio of the carrier to the lipid being in the range of from 5:1 to 1:15;

(ii) forming discrete units of the suspension or solution; and (iii) removing the solvent from the discrete units under conditions whereby unit dosages are formed comprising a network of carrier/filler carrying a dosage of the pharmaceutically active substance in association with the lipid.

2. A process as claimed in claim 1 wherein the lipid is a wax, a saturated or non-saturated fatty acid or a derivative thereof, a lecithin, phospholipid or lysophoscholipid, a glycolipid, a sterol, an oil, a hydrogenated vegetable oil, a fatty hydrocarbon or alcohol, or a mixture thereof.

3. A process as claimed in claim 1 wherein the lipid is a wax, a saturated or non-saturated fatty acid or a derivative thereof, a triglyceride, an oil, or a $C_{10}$–$C_{30}$ aliphatic alcohol.

4. A process as claimed in claim 3 wherein the lipid is stearic acid or a derivative thereof.

5. A process as claimed in claim 1 wherein the lipid is a lecithin or phospholipid or a glycolipid.

6. A process as claimed in claim 1 wherein the lipid is a sterol.

7. A process as claimed in claim 1 wherein the carrier is present in the solution or suspension in an amount of from 1 to 6% by weight based on the weight of the solution or suspension.

8. A process as claimed in claim 1 wherein the carrier is gelatin.

9. A process as claimed in claim 1 wherein the filler is present in the solution or suspension in an amount of from 1 to 6% by weight based on the weight of the solution or suspension.

10. A process as claimed in claim 1 wherein the filler is mannitol.

11. A process as claimed in claim 1 wherein the pharmaceutically active substance is incorporated into the solution or suspension in an amount sufficient to provide up to 100 mg per unit dosage.

12. A process as claimed in claim 1 wherein the lipid is incorporated into the solution or suspension in an amount sufficient to provide up to 250 mg per unit dosage.

13. A process as claimed in claim 1 wherein the solvent comprises water.

14. A process as claimed in claim 13 wherein the solvent further comprises a co-solvent.

15. A process as claimed in claim 1 wherein the discrete units are liquid, frozen or gelled units.

16. A process as claimed in claim 1 wherein the discrete units are formed in a mould comprising a plurality of pockets.

17. A process as claimed in claim 15 wherein the discrete units are liquid units which are frozen prior to removal of the solvent.

18. A process as claimed in claim 15 wherein the units are frozen units and the solvent is removed by freeze drying.

19. A process as claimed in claim 15 wherein the units are frozen units and the solvent is removed by contacting the frozen matrix comprising the first solvent, the pharmaceutically active substance and the carrier material with a second solvent that is substantially miscible with the first solvent at a temperature lower than the solidification point of the first solvent, whereby the first solvent is removed from the matrix.

20. A process as claimed in claim 15 wherein the units are frozen units and the solvent is removed by vacuum drying under conditions whereby the solvent is evaporated from the frozen units through the liquid phase to a gas.

21. A process as claimed in claim 15 wherein the discrete units are gelled units from which the solvent is removed by drying under decreased pressure or by forced-air drying.

22. A process as claimed in claim 16 wherein the mould comprises one or more depressions is a sheet of a filmic material.

23. A process as claimed in claim 22 wherein a sheet of a covering material is adhered to the filmic material in the area around the depression or depressions after the removal of solvent from the solution or suspension.

24. A process as claimed in claim 1 wherein the pharmaceutically active substance is an antacid, analgesic, anti-anginal, anti-anxiety, anti-arrhythmic, anti-bacterial, anti-diarrhoeal, anti-depressant, anti-epileptic, anti-fungal, anti-histamine, anti-hypertensive, anti-inflammatory agent, anti-viral, cardiac agent, contraceptive, cough suppressant, cytotoxic, decongestant or diuretic drug, a genito-urinary drug a drug for use in parkinsonism or related disorders a drug for use in rheumatic disorders, a hypnotic, mineral, vitamin, lipid lowering drug or sex hormone.

25. An oral solid rapidly disintegrating dosage form of a pharmaceutically active substance whenever prepared by a process as claimed in claim 1.

26. An oral solid rapidly disintegrating dosage form of a pharmaceutically active substance with an unacceptable taste which comprises a network of a carrier/filler material carrying a dosage of the said pharmaceutically active substance in association with a lipid.

27. An oral dosage form as claimed in claim 26 wherein the carrier is gelatin.

28. An oral dosage form as claimed in claim 26 wherein the filler is mannitol.

29. An oral dosage form as claimed in claim 26 wherein the lipid is a wax, a saturated or non-saturated fatty acid or a derivative thereof, a lecithin, phospholipid or lysophospholipid, a glycolipid, a sterol, an oil, a hydrogenated vegetable oil, a fatty hydrocarbon or alcohol, or a mixture thereof.

30. An oral dosage form as claimed in claim 29 wherein the lipid is a wax, a saturated or non-saturated fatty acid or a derivative thereof, a triglyceride, an oil, or a $C_{10}$–$C_{30}$ aliphatic alcohol.

31. An oral dosage form as claimed in claim 30 wherein the lipid is stearic acid or a derivative thereof.

32. An oral dosage form as claimed in claim 29 wherein the lipid is a lecithin or phospholipid or a glycolipid.

33. An oral dosage form as claimed in claim 29 wherein the lipid is a sterol.

34. An oral dosage form as claimed in claim 26 wherein the pharmaceutically active substance is an antacid, analgesic, anti-anginal, anti-anxiety, anti-arrhythmic, anti-bacterial, anti-diarrhoeal, anti-depressant, anti-epileptic, anti-fungal, anti-histamine, anti-hypertensive, anti-inflammatory agent, anti-viral, cardiac agent, contraceptive, cough suppressant, cytotoxic, decongestant or diuretic drug, a genito-urinary drug a drug for use in parkinsonism or related disorders a drug for use in rheumatic disorders, a hypnotic, mineral, vitamin, lipid lowering drug or sex hormone.

* * * * *